United States Patent
Elku et al.

(10) Patent No.: US 8,167,654 B2
(45) Date of Patent: *May 1, 2012

(54) RADIATION LAMP AND RADIATION SOURCE MODULE INCORPORATING SAME

(75) Inventors: Joseph Elku, Tillsonburg (CA); Jim Fraser, St. Thomas (CA); Richard Gratton, London (CA)

(73) Assignee: Trojan Technologies (CA)

( * ) Notice: Subject to any disclaimer, the term of this patent is extended or adjusted under 35 U.S.C. 154(b) by 0 days.

This patent is subject to a terminal disclaimer.

(21) Appl. No.: 12/098,363

(22) Filed: Apr. 4, 2008

(65) Prior Publication Data

US 2008/0182455 A1 Jul. 31, 2008

Related U.S. Application Data

(63) Continuation of application No. 11/626,756, filed on Jan. 24, 2007, now Pat. No. 7,390,225, which is a continuation-in-part of application No. PCT/CA2006/001040, filed on Jun. 27, 2006.

(60) Provisional application No. 60/693,502, filed on Jun. 24, 2005.

(51) Int. Cl.
*H01K 1/00* (2006.01)
(52) U.S. Cl. ...................................... 439/617
(58) Field of Classification Search .................. 439/617, 439/611, 682, 683
See application file for complete search history.

(56) References Cited

U.S. PATENT DOCUMENTS

| | | | | |
|---|---|---|---|---|
| 2,869,104 A * | 1/1959 | Pleak | | 439/617 |
| 4,070,084 A | 1/1978 | Hutchison | | |
| 5,166,527 A | 11/1992 | Solymar | | |
| 1,965,127 A * | 2/1997 | Devlin et al. | | 439/144 |
| 5,645,449 A * | 7/1997 | Sabo | | 439/540.1 |
| 6,220,891 B1* | 4/2001 | Hils | | 439/482 |
| 6,254,252 B1 | 7/2001 | Coushaine et al. | | |
| 6,354,843 B1 | 3/2002 | Kato | | |
| 6,488,510 B2 | 12/2002 | Li | | |
| 7,033,203 B2* | 4/2006 | Titchener | | 439/369 |
| 7,390,222 B2* | 6/2008 | Ciancanelli et al. | | 439/617 |
| 7,390,225 B2* | 6/2008 | Elku et al. | | 439/660 |
| 2002/0168881 A1 | 11/2002 | Hwang et al. | | |

FOREIGN PATENT DOCUMENTS

| | | |
|---|---|---|
| EP | 0 281 079 A2 | 9/1988 |
| JP | 62-115625 A | 5/1987 |
| WO | 2004/108604 A1 | 12/2004 |

OTHER PUBLICATIONS

International Search Report for International Application No. PCT/CA2006/001040, published as WO 2006/13026 A1 on Dec. 28, 2006.

(Continued)

*Primary Examiner* — Tulsidas C Patel
*Assistant Examiner* — Phuong Nguyen
(74) *Attorney, Agent, or Firm* — Katten Muchin Rosenman LLP

(57) ABSTRACT

There is disclosed a lamp device including a longitudinal axis, a first elongate electrical connector and a second elongate electrical connector, each of the first elongate electrical connector and the second elongate connector being non-parallel with respect to the longitudinal axis. The present lamp device provides a reliable electric connection on the one hand, yet is relatively inexpensive, uncomplicated and simple to implement on the other hand.

24 Claims, 14 Drawing Sheets

OTHER PUBLICATIONS

Jan. 10, 2008 Transmittal and International Preliminary Report on Patentability for International Application No. PCT/CA2006/001040, which was published as WO 2006/13026 A1 on Dec. 28, 2006.

Examiner's first report on Australian Patent Application No. 2006261548, with a mailing date of Oct. 29, 2010.

Office Action for Canadian Patent Application No. 2,613,147, with a mailing date of Mar. 11, 2010.

The Second Office Action for People's Republic of China Patent Application No. 200680022615.8, with a mailing date of Jun. 21, 2010.

Office Action for Russian Patent Application No. 2008102161/07(002365).

* cited by examiner

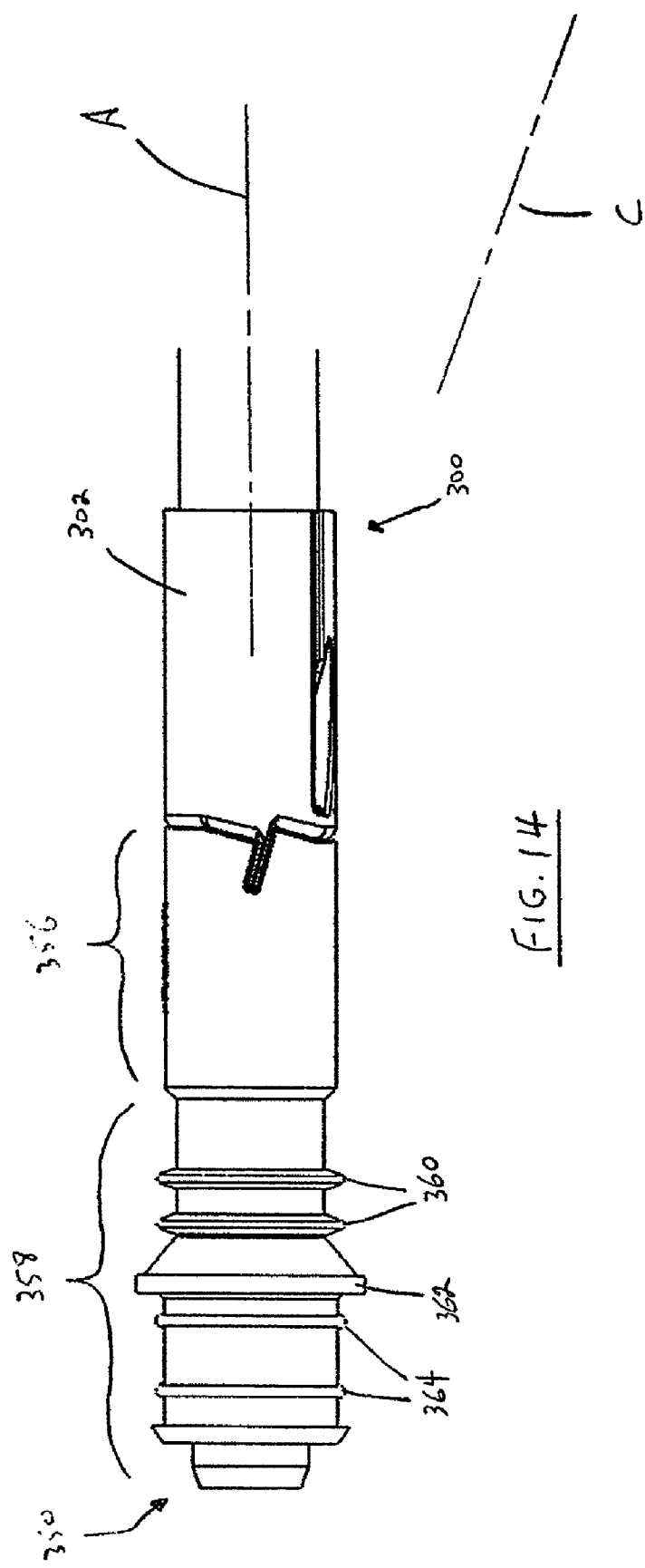

RADIATION LAMP AND RADIATION SOURCE MODULE INCORPORATING SAME

CROSS-REFERENCE TO RELATED APPLICATIONS

The present application is a continuation of U.S. patent application Ser. No. 11/626,756, filed Jan. 24, 2007, which is a continuation-in-part of International Patent Application No. PCT/CA2006/001040, with an international filing date of Jun. 27, 2006, which claims priority under 35 U.S.C. §119(e) to U.S. Provisional Patent Application No. 60/693,502, filed Jun. 24, 2005, the entire contents of each of which are incorporated by reference herein.

BACKGROUND OF THE INVENTION

1. Field of the Invention

In one of its aspects, the present invention relates to a lamp device. In another of its aspects, the present invention relates to a radiation lamp. In yet another of its aspects, the present invention relates to a radiation source assembly. In yet another of its aspects, the present invention relates to a radiation source module. In yet another of its aspects, the present invention relates to a fluid treatment system. In yet another of its aspects, the present invention relates to a water disinfection system.

2. Background Information

Fluid treatment systems such as water disinfection systems are generally known in the art.

See, for example, one or more of the following U.S. Pat. Nos.:

Re36,896,
3,418,370,
4,482,809,
4,872,980,
5,006,244,
5,471,063,
5,504,355,
5,538,210,
6,342,188,
6,500,346,
6,507,028,
6,646,269,
6,674,084,
6,803,586, and
6,863,078.

Many of the above-identified United States patents teach fluid treatment systems that employ ultraviolet (UV) radiation to kill, sterilize and/or prevent replication of microorganisms (bacteria, viruses, pathogens and the like) that may be present in the fluid.

Generally, such conventional fluid treatment systems employ an ultraviolet radiation lamp to emit radiation of a particular wavelength or range of wavelengths (usually between 185 and 400 nm) to kill, sterilize and/or prevent replication of microorganisms (bacteria, viruses, pathogens and the like) that may be present in the fluid.

Conventional ultraviolet radiation lamps include low pressure lamps, medium pressure lamps, low pressure high output lamps and the like.

In more recent years, it has become conventional to use such ultraviolet lamps configured to have all of the electrical connections disposed at one end of the lamp. See, for example, FIGS. 2-8 of U.S. Pat. No. 4,700,101 [Ellner, et al. (Ellner)] and FIGS. 1, 2 and 4 of U.S. Pat. No. 5,166,527 [Solymar].

As can be seen from the conventional radiation lamps taught by Ellner and Solymar, the electrical connection pins are elongate and are disposed such that the axes of the pins are parallel with the longitudinal axes of radiation lamp. In other words, the electrical connection is made by pushing an end cap or other connection base on to the pins in a direction parallel to the longitudinal axis of the radiation lamp.

The problem with this approach is that in many applications, the radiation lamp is immersed in a flow of water and turbulence created within that water treatment system invariably imparts a vibratory motion to the lamps which frequently results in lamps being vibrated or shaken loose of its electrical connection base or socket thereby causing the lamps to be rendered completely or intermittently inoperative. When such an event occurs, the water being treated may not be fully disinfected.

More recently, other attempts to address this problem have used a relatively complicated mechanical connection (e.g., a so-called "push-and-twist" connection) to secure the lamp to the connection base. See, for example, U.S. Pat. No. 5,422,487 [Sauska, et al. (Sauska)] and U.S. Pat. No. 6,884,103 [Kovacs]. The problem with these approaches is the complexity of the mechanical connection between the lamp and the base unit requiring the use of springs, specialized connection lugs and the like. Further, a connection system which is predicated on a dual motion system such that pushing and twisting gives rise to a higher incidents of lamp breakage and other damage to the module by field personal.

Accordingly, there remains the need in the art for a lamp device, particularly a radiation lamp, which will provide a reliable electric connection on the one hand, yet be relatively inexpensive, uncomplicated and simple to implement on the other hand.

SUMMARY OF THE INVENTION

It is an object of the present invention to obviate or mitigate at least one of the above-mentioned disadvantages of conventional fluid treatment systems.

Accordingly, in one of its aspects, the present invention provides a lamp device comprising a longitudinal axis, a first elongate electrical connector and a second elongate electrical connector, each of the first elongate electrical connector and the second elongate connector being non-parallel with respect to the longitudinal axis.

In another of its aspects, the present invention relates to a radiation source assembly comprising such a lamp device, together with a radiation transparent protective sleeve.

In another of its aspects, the present invention provides a radiation lamp comprising: an elongate radiation-emitting cavity having a longitudinal axis; a first electrical connection base disposed at a first end of the elongate radiation-emitting cavity; a pair of first elongate electrical connectors and a pair of second elongate electrical connectors disposed in the first electrical connection base; each of the first elongate electrical connector and the second elongate connector being non-parallel with respect to the longitudinal axis.

In yet another of its aspects, the present invention provides a radiation source module comprising such a radiation lamp and a first support member for supporting the radiation lamp, the first support member comprising a second electrical connection base for engagement with the first electrical connection base and connection to a power supply.

Other aspects of the present invention relate to fluid treatment systems and water disinfection systems incorporating the above lamp device, radiation source assembly, radiation lamp and radiation source module, respectively.

BRIEF DESCRIPTION OF THE DRAWINGS

Embodiments of the present invention will be described with reference to the accompanying drawings, wherein like reference numerals denote like parts, and in which:

FIGS. 9-14 illustrate portions of a third preferred embodiment of the present lamp device.

DETAILED DESCRIPTION OF THE PREFERRED EMBODIMENTS

Figure 1:
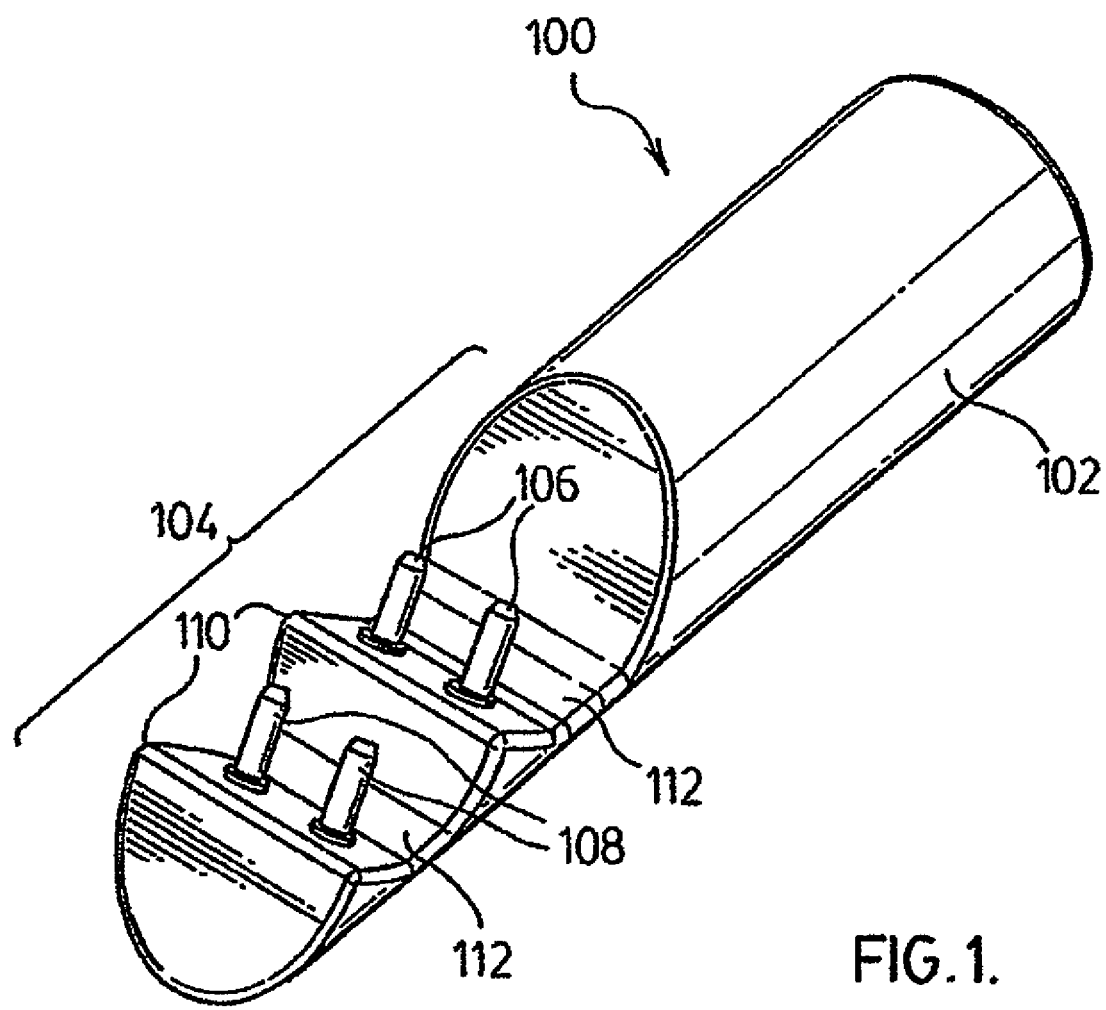
FIGS. 1-4 illustrate components of a first preferred embodiment of the present lamp device.

Preferred embodiments of the present invention will be described below with reference to FIGS. 1-14. In FIGS. 1-14, there is shown in detail the electrical connection portion of a radiation lamp and/or the connection thereof to a complementary base unit. The remaining detail of the lamp is not shown for easier understanding. However, those of skill in the art will readily recognize how the specific connection shown in the Figures can be implemented in a lamp design by reference to the various prior art patents referred to above.

With reference to FIGS. 1-4, there is illustrated a first electrical base unit 100 and a second electrical base unit 150.

First electrical connection base unit 100 comprises a housing 102. An end portion 104 of unit 100 comprises a first pair of electrical connectors 106 and a second pair of electrical connectors 108.

End portion 104 comprises an undulating shape having a series of peaks 110 and valleys 112. Electrical connectors 106, 108 are connected to wire or other suitable electrical conveyance (not shown) disposed within housing 102 which is then connected to the radiation-emitting cavity of the lamp in a conventional manner.

Figure 2:
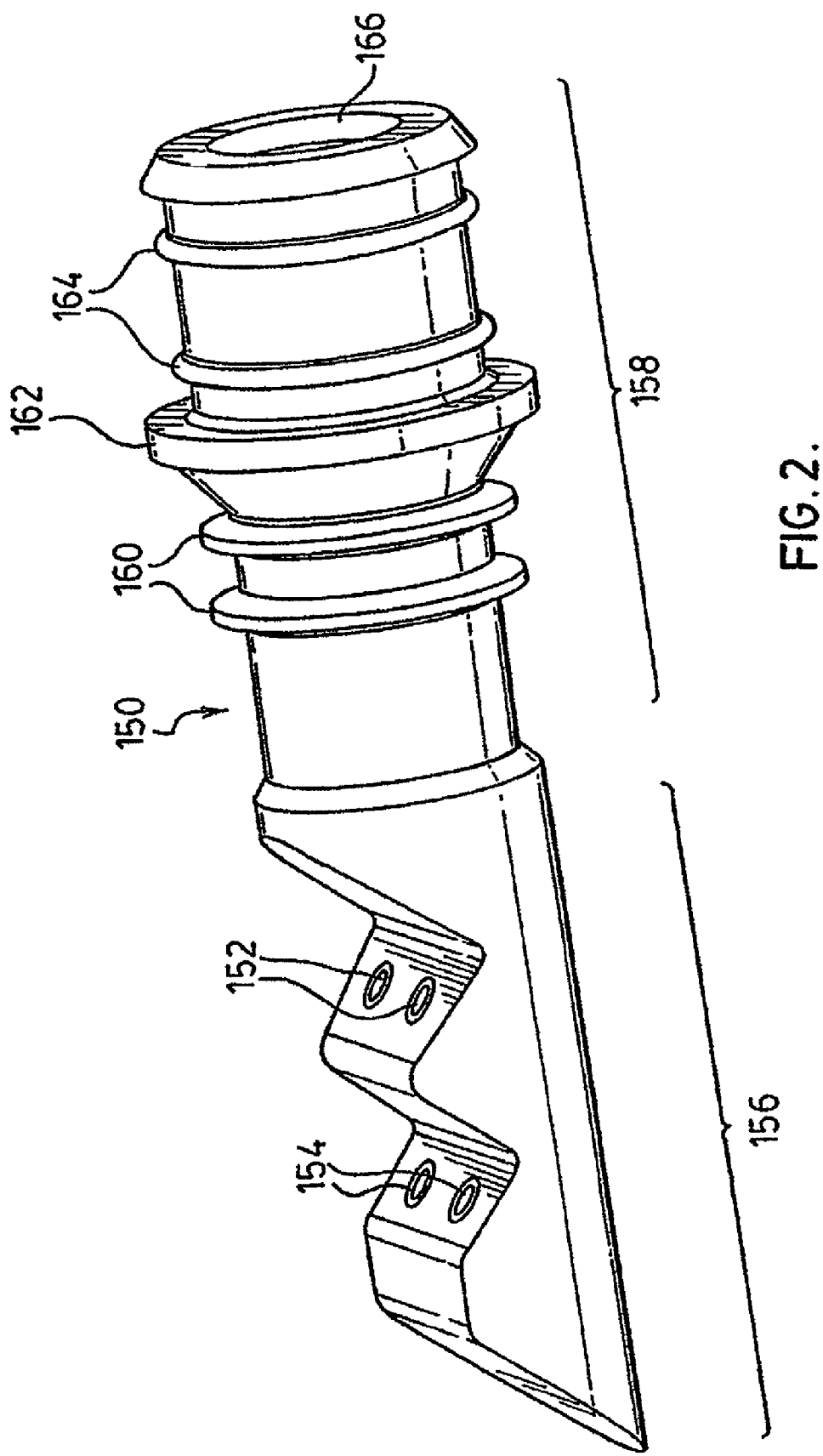

With particular reference to FIG. 2, there is illustrated an enlarged view of base unit 150. As shown, base unit 150 comprises a first pair of electrical receptacles 152 and a second pair of electrical receptacles 154. These receptacles are disposed at a first end portion 156 of base unit 150. Disposed at another end portion 158 of base unit 150 is a sealing system which functions in a manner similar to that described in U.S. Pat. Nos. 4,872,980 and 5,006,244 referred to above. Specifically, end portion 158 comprises a pair of annular seals 160 that serve to seal the interior of a radiation transparent protective sleeve (FIG. 4) placed over the radiation lamp.

Also disposed on end portion 158 is a stop portion 162 that serves as stop for the open end of protective sleeves surrounding the lamp.

Portion 158 further comprises a pair of annular seals 164 that serve to seal against water ingress into the frame of a module in which the lamp is placed (again, reference can be made to U.S. Pat. Nos. 4,872,980 and 5,006,244 for further details on the function of the seals).

Electrical receptacles 152, 154 are wired in a conventional manner with the electrical wires or other electrical conveyance emerging from an aperture 166 in end portion 158 connection unit 150.

Figure 3:
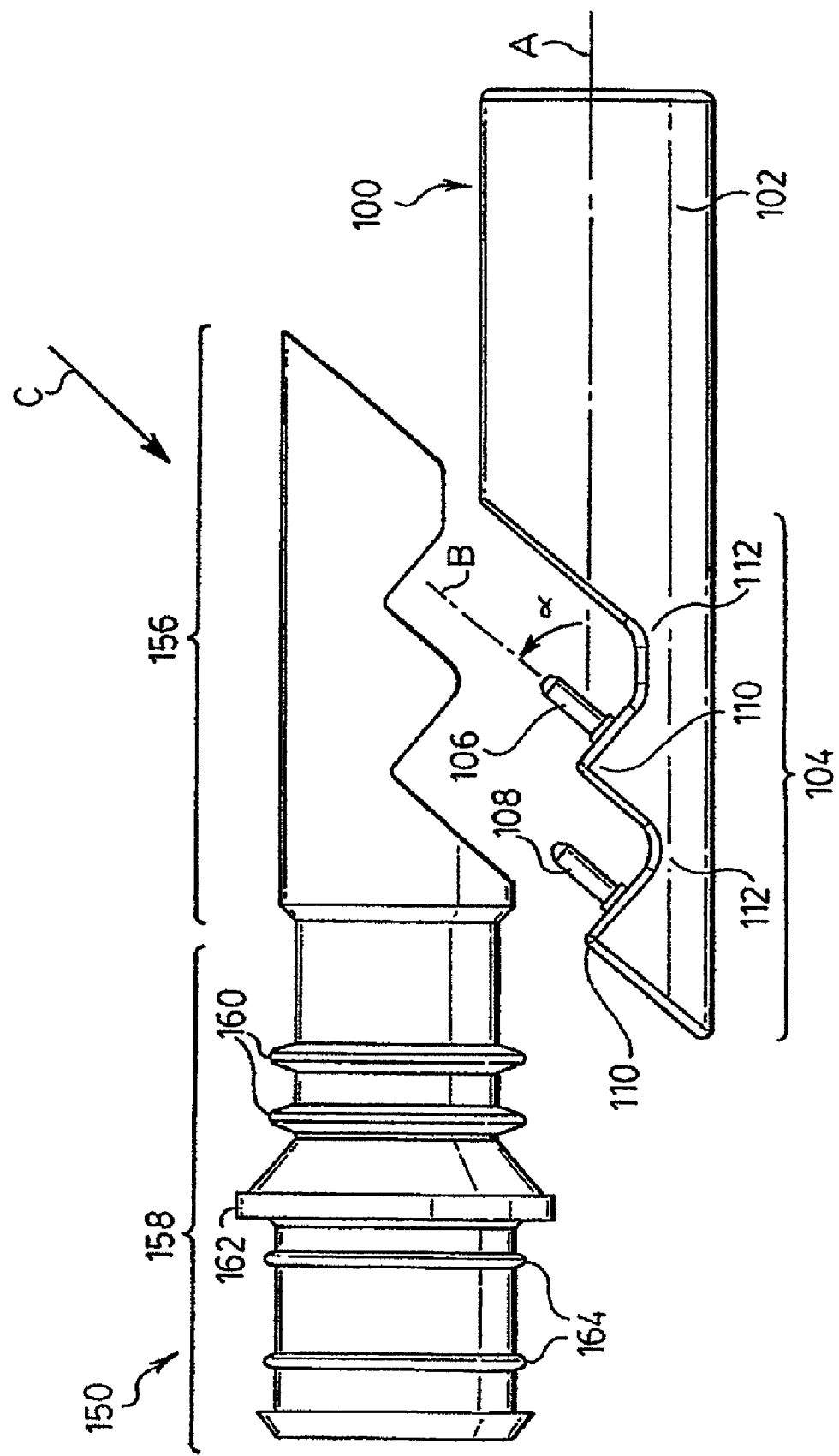

With particular reference to FIG. 3, it will be seen that when base unit 100 is connected to the remaining components of the radiation lamp, there will be a longitudinal axes shown at line A through base unit 100 and the remainder of the lamp. Further, it will be seen that electrical connectors 106, 108 are elongate and have a longitudinal axis through line B. An important feature of this preferred embodiment is that line B is non-parallel with respect to line A. In other words, the longitudinal axis through each of electrical connectors 106, 108 is in a non-parallel relationship with the longitudinal axis through base unit 100 and the remainder of the radiation lamp. In the specific embodiment shown, electrical connectors 106, 108 are disposed at an acute angle α toward the radiation-emitting cavity (not shown) of the lamp.

Figure 4:
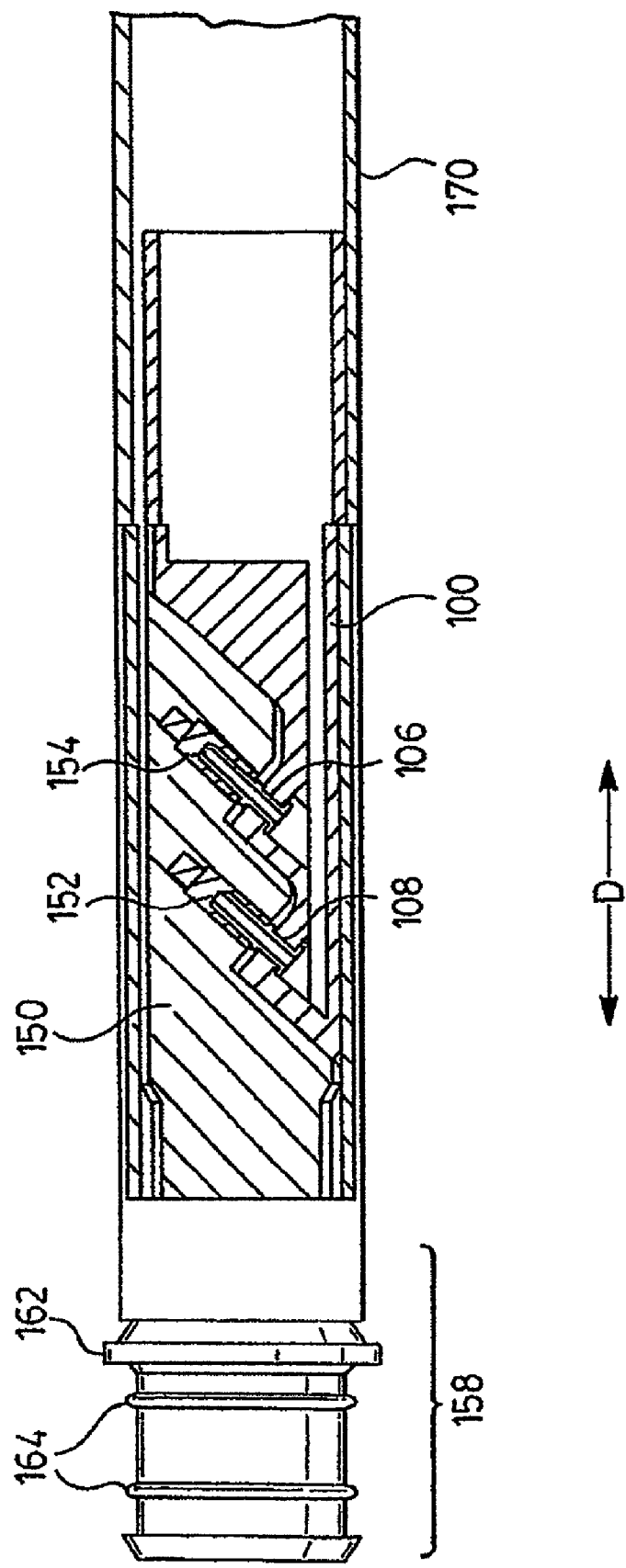
Figure 5:
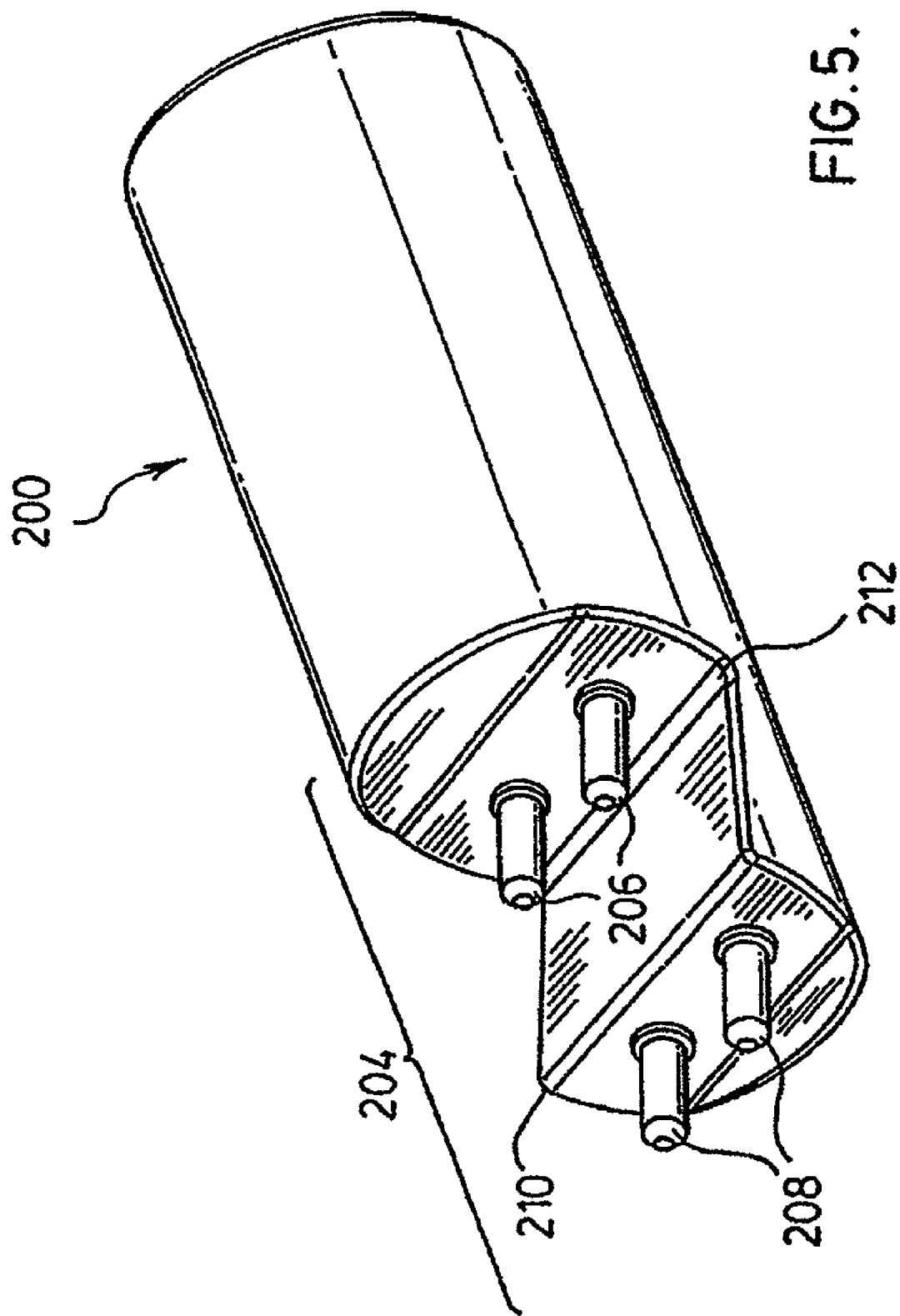
FIGS. 5-8 illustrate portions of a second preferred embodiment of the present lamp device.
Figure 6:
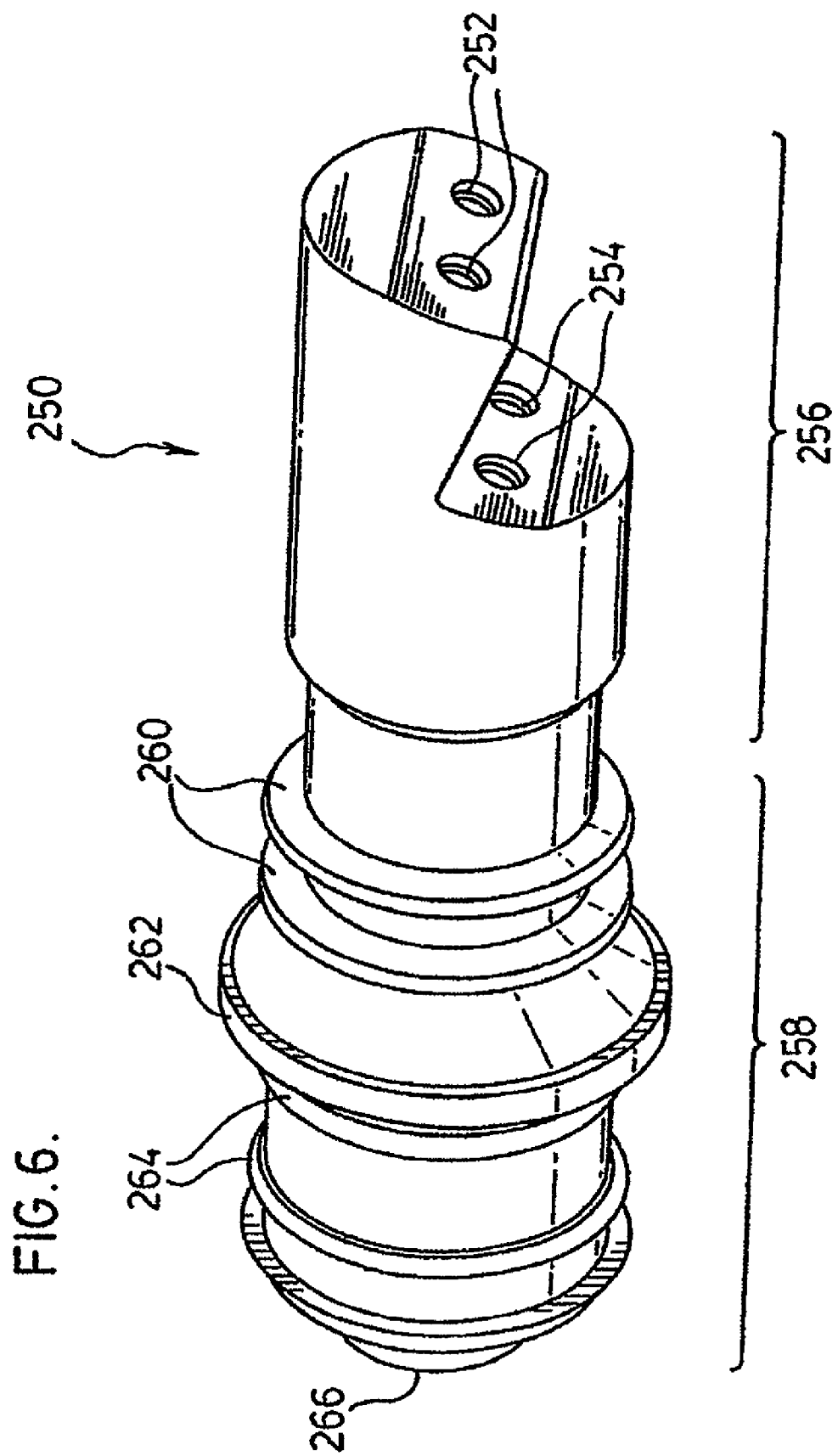
Figure 7:
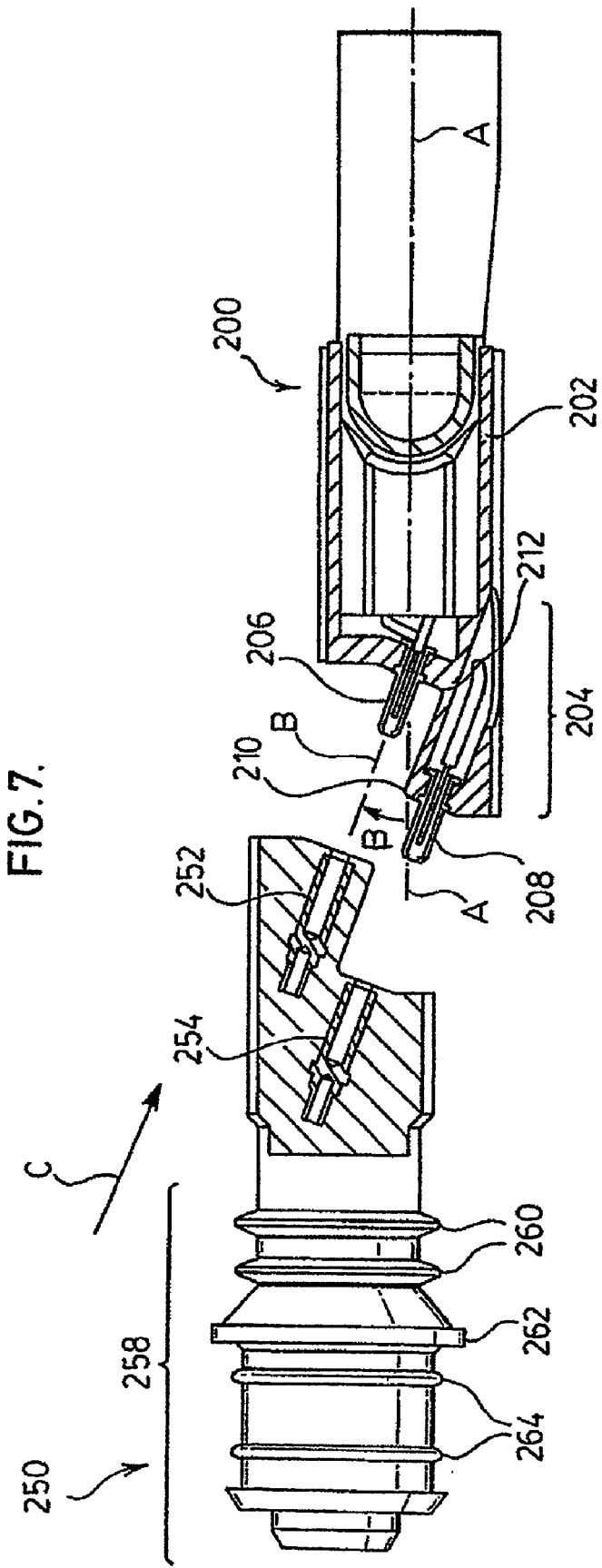
Figure 8:
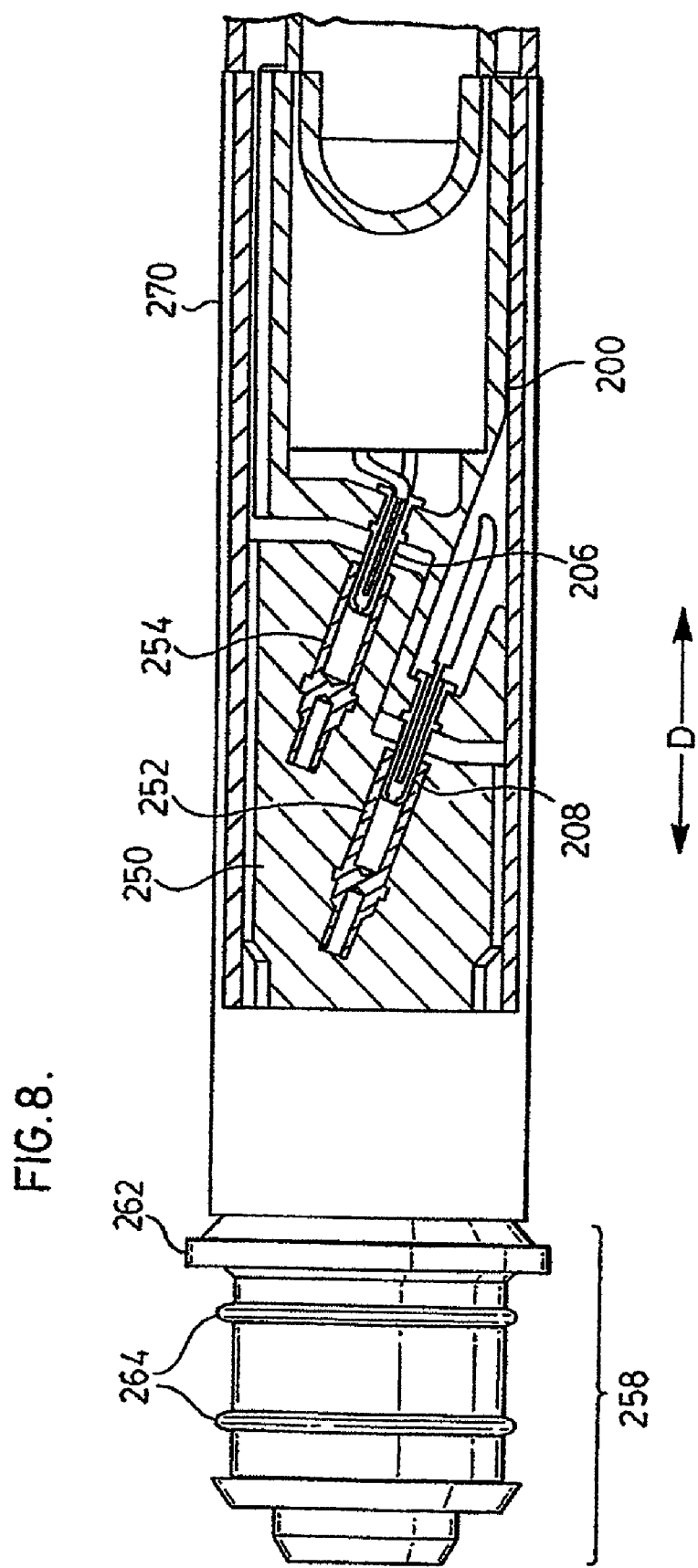
Figure 9:
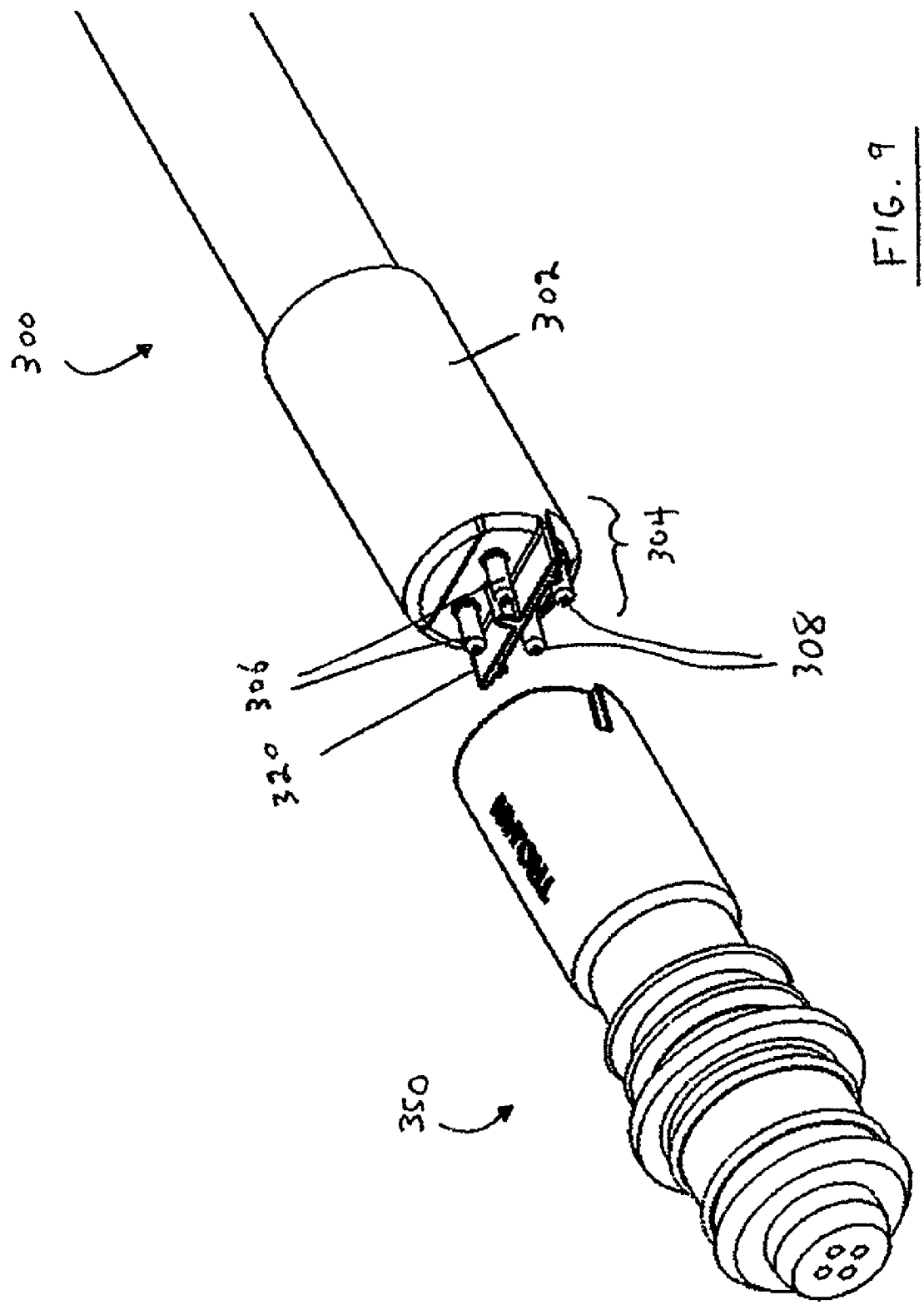
Figure 10:
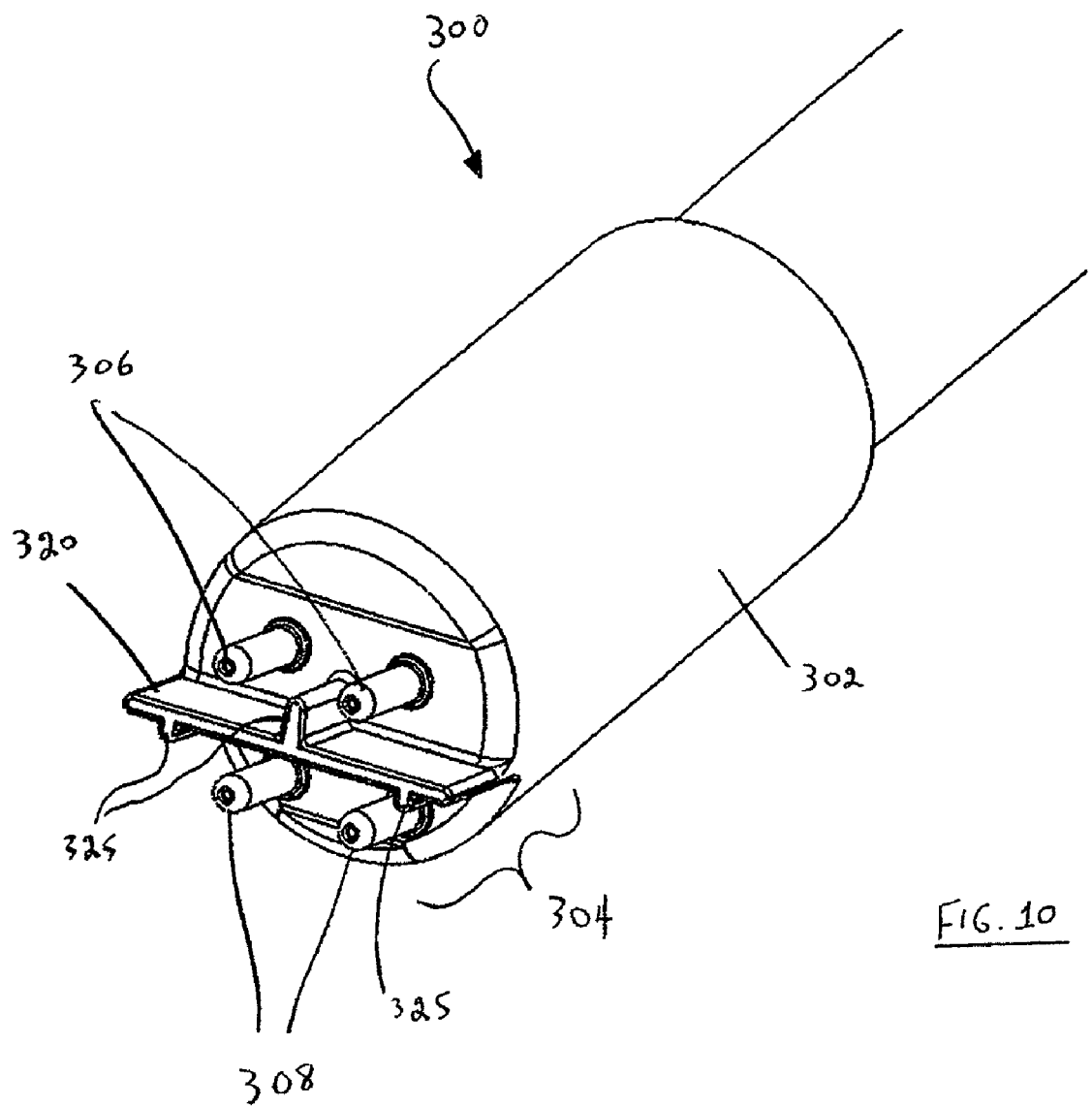

When it is desired to engage base unit 100 with base unit 150, the base units are aligned as shown in FIG. 3 and moved with respect to one another in the direction of arrow C. The engaged components are shown in FIG. 4 and a radiation transparent protective sleeve 170 encases the connected units 100 and 150. As will be appreciated by those of skill in the art, once the connection is shown as made in FIG. 4, the connection will withstand vibration forces conveyed to the radiation lamp. Specifically, base unit 100 will not separate from base unit 150 in a direction of arrow D, particularly when radiation transparent protective sleeve 170 is disposed over the connection.

With reference to FIGS. 5-8, there is illustrated a second embodiment of the preferred invention. In the description of FIGS. 5-8, reference numerals will be used wherein the last two digits correspond to the same element appearing in FIGS. 1-4 and the first numeral will be "2" in FIGS. 5-8 instead of "1" in FIGS. 1-4. Thus, it will be seen that a first major difference between the two embodiments is that the embodiment illustrated in FIGS. 5-8 comprises electrical connectors 206, 208 that are angled away (β) from the radiation-emitting cavity. Another difference is that the cross-sectional shape base unit 200 in FIGS. 5-8 comprises a single valley 212 instead of the pair of valleys 112 in the embodiment illustrated in FIGS. 1-4. Yet another difference is that the cross-sectional shape base unit 200 in FIGS. 5-8 comprises a single peak 210 instead of the pair of valleys 110 in the embodiment illustrated in FIGS. 1-4. Otherwise, the embodiment shown in FIGS. 5-8 may be used in a manner similar to that described above with respect to FIGS. 1-4.

With reference to FIGS. 9-14, there is illustrated a third preferred embodiment of the present lamp device. More particularly, there is illustrated a first electrical base unit 300 and a second electrical base unit 350.

First electrical base unit 300 comprises a housing 302. An end portion 304 of first electrical base unit 300 comprises a first pair of electrical connectors 306 and a second pair of electrical connectors 308.

Electrical connectors 306, 308 are connected to wire or other suitable electrical conveyance (not shown) disposed within housing 302 which is then connected to the radiation-emitting cavity of the lamp in conventional manner.

End portion 304 of housing 302 further comprises a fin portion 320 which is disposed in a manner that separates electrical connectors 306 from electrical connectors 308. Fin portion 320 comprises a series of rib portions 325 which serve to support fin portion 320.

Fin portion 320 acts as a dielectric barrier so as to obviate or mitigate arcing between electrical connectors 306 and electrical connectors 308. The use of fin member 320 and rib portions 325 is optional.

With particular reference to FIG. 12, there is illustrated a view of base unit 350. Base unit 350 is very similar in its design and function to base unit 150 described above with reference to FIGS. 1-4. In the description of FIGS. 9-14, reference numerals are used wherein the last two digits correspond to the same element appearing in FIGS. 1-4, and the first numeral will be "3" in FIGS. 9-14 instead of "1" in FIGS. 1-4.

The main difference between electrical base unit 350 in FIGS. 9-14 and electrical base unit 150 in FIGS. 1-4 is the provision in base portion 350 of a receptacle portion 351 that has a substantially complementary shape to the combination of fin portion 320 and rib portions 325 disposed in end portion 304 of electrical base unit 350.

Figure 11:
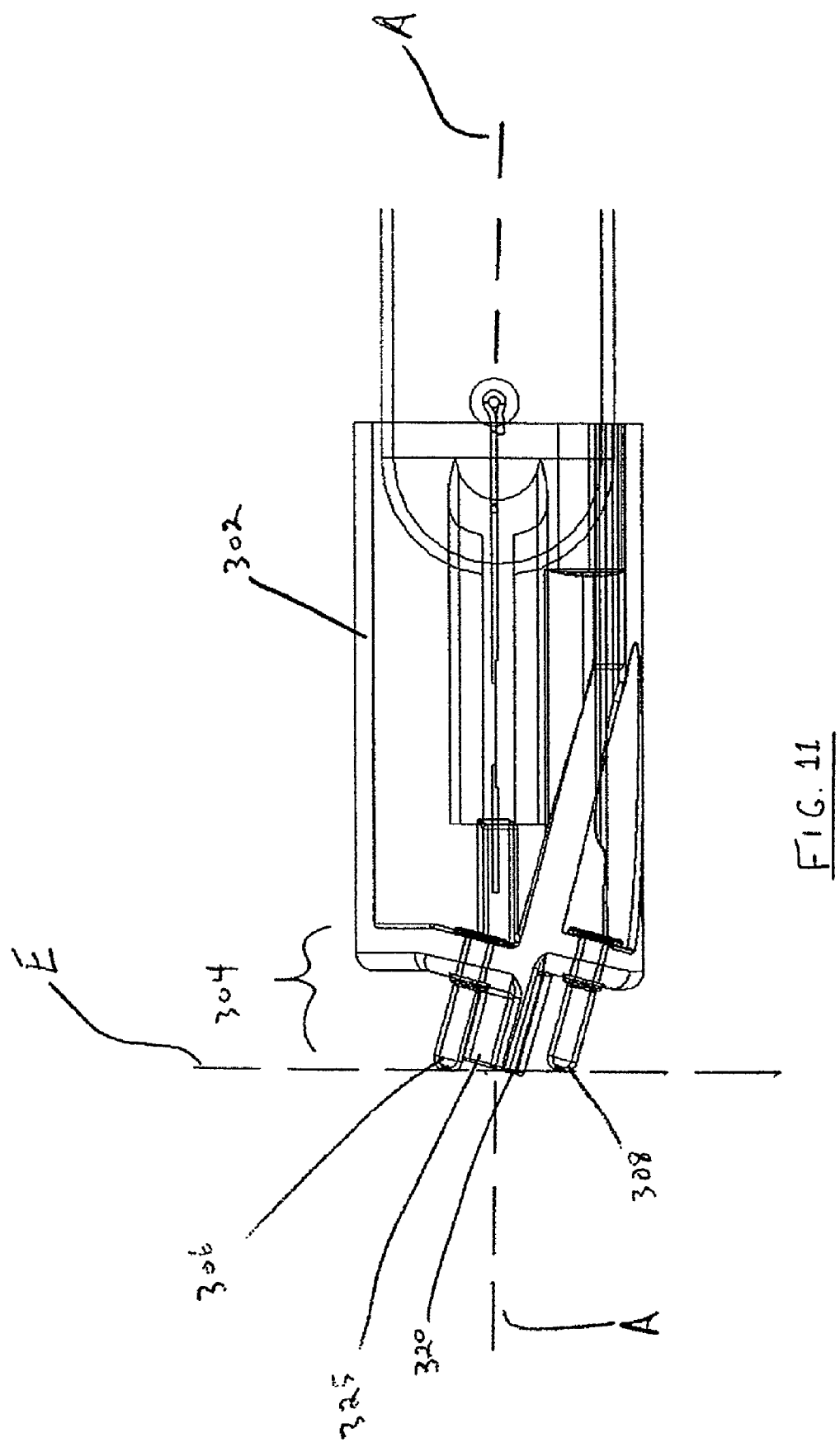
Figure 19:
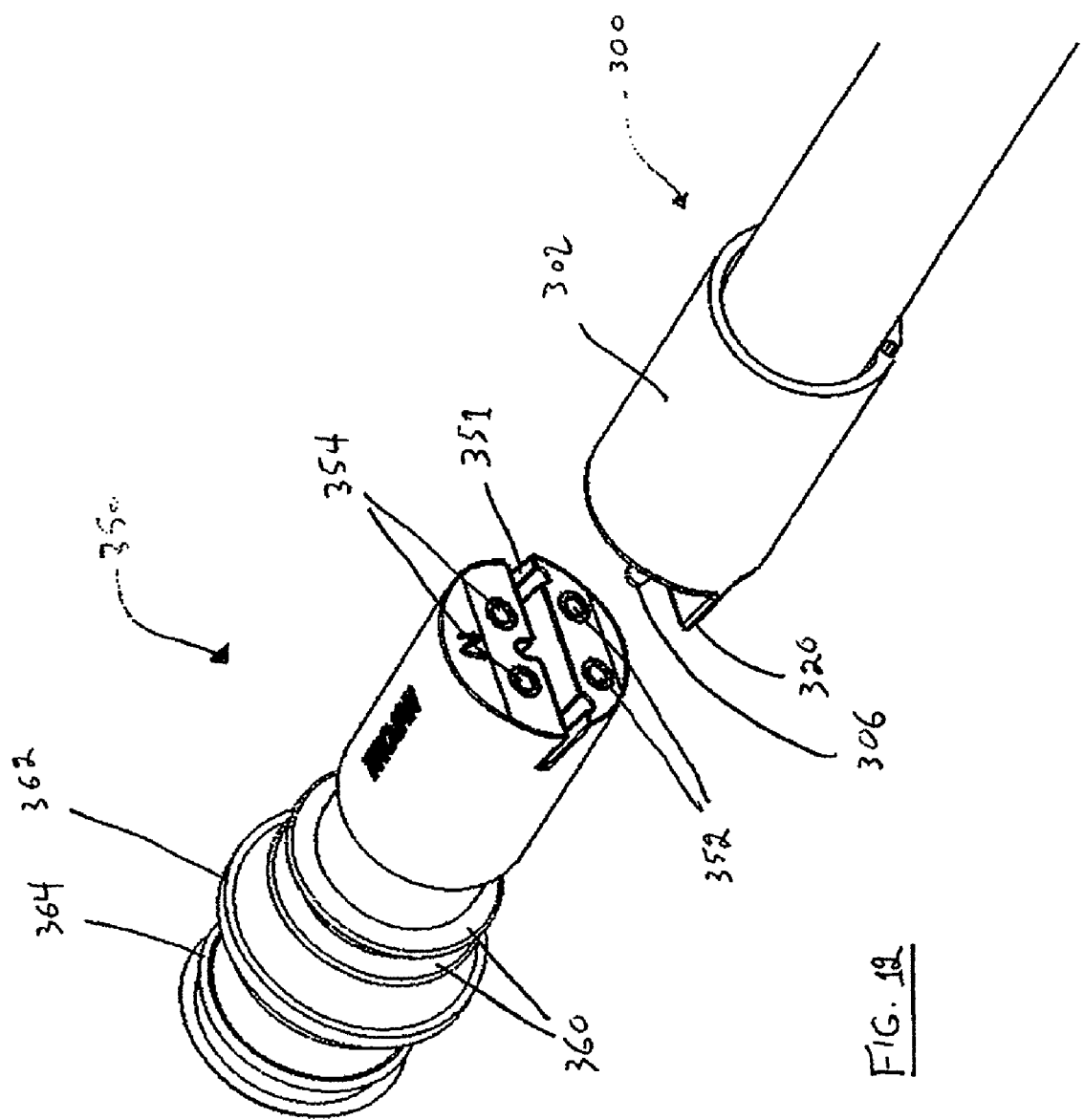
Figure 13:
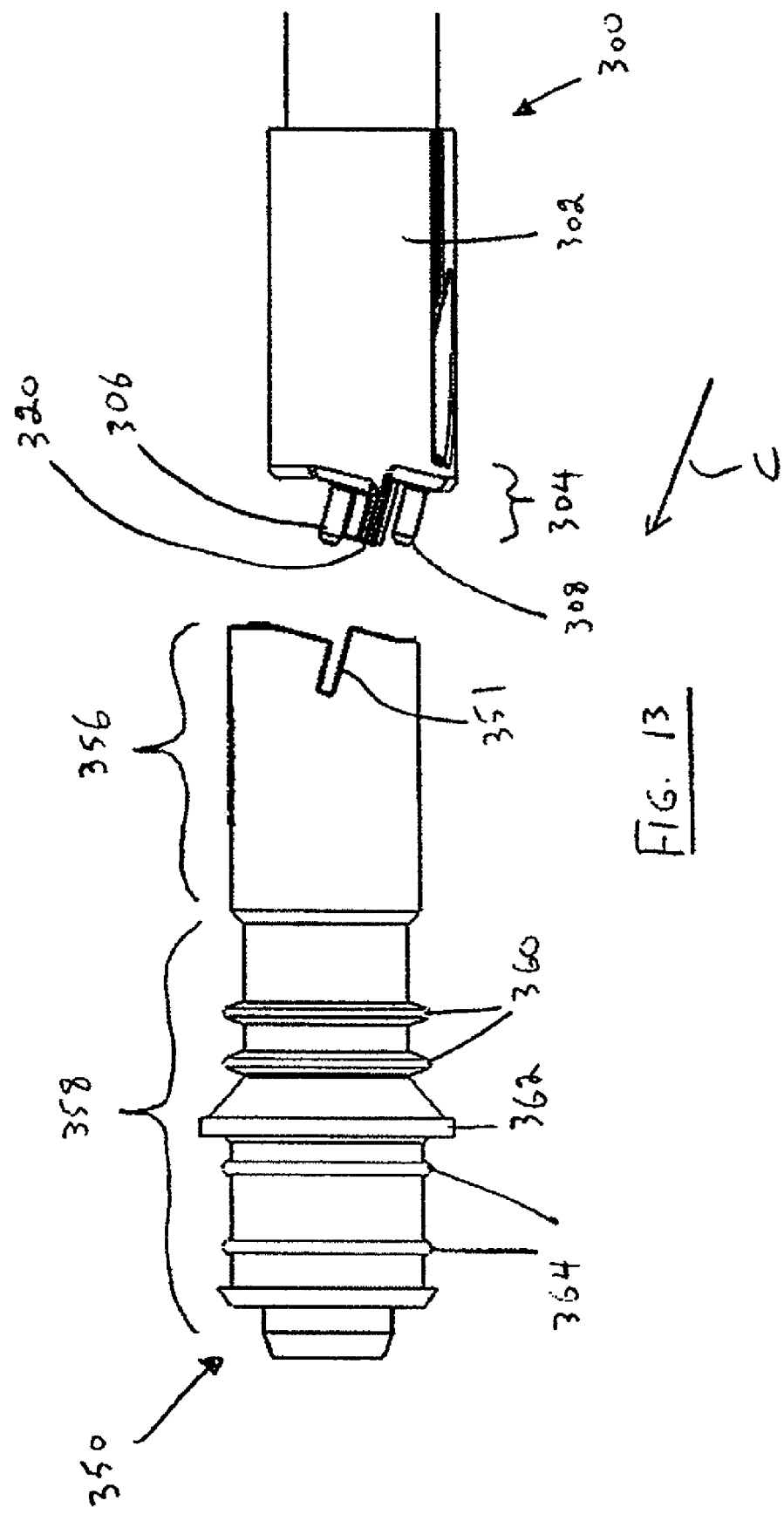

With particular reference to FIGS. 11 and 14, it can been seen that a difference between the embodiments of the present invention described above with reference to FIGS. 1-8 and the embodiment illustrated in FIGS. 9-14 is the relative orientation of the electrical connectors. Specifically, in the embodiment illustrated in FIG. 1, electrical connectors 106 and 108 are disposed in an offset manner with respect to line A (FIG. 3)—i.e., the longitudinal axis. A similar arrangement exists in the embodiment illustrated in FIGS. 5-8 wherein electrical connectors 206 are offset longitudinally with respect to electrical connectors 208.

In contrast, it can be seen that electrical connectors 306 are not offset with respect to electrical connectors 308 along line A (FIG. 11) in the embodiment illustrated in FIGS. 9-14. Thus, the distal ends of electrical connectors 306 and electrical connectors 308 are in substantial alignment along line E in FIG. 11.

With reference to FIG. 14, it can be seen that first electrical base unit 300 cannot be disengaged from second electrical base unit 350 along line A. Thus, when lamp device incorporating first electrical base unit 300 and second electrical base unit 350 is disposed in a protective (e.g., quartz) sleeve having a diameter very similar to that of stop portion 362, first electrical base unit 300 can not be disengaged from second electrical base unit 350 in a direction along line A. Rather, the two base units may be disengaged by relative movement thereof in the direction of line C (i.e., after removal of the protective sleeve).

While this invention has been described with reference to illustrative embodiments and examples, the description is not intended to be construed in a limiting sense. Thus, various modifications of the illustrative embodiments, as well as other embodiments of the invention, will be apparent to persons skilled in the art upon reference to this description. For example, it is possible to reverse the arrangement of electrical connectors and electrical receptacles in the illustrated embodiments—i.e., the electrical connectors would be disposed in electrical connection base unit 150,250,350 and the electrical receptacles would be disposed in electrical connection base unit 100,200,300. Also, it is possible to have a mixture of electrical connectors and electrical receptacles on electrical connection base unit 100,200,300 and a complementary mixture of electrical connectors and electrical receptacles on electrical connection base unit 150,250,350. Yet another possible modification of the illustrated embodiments relates to disposing the electrical connectors such that the longitudinal axis of the electrical connectors is substantially orthogonal to the longitudinal axis of the radiation lamp (i.e., $\alpha \approx 90°$ and $\beta \approx 90°$). Yet another modification of the illustrated embodiments relates to the use of electrical connection bases that, in cross-section, contain no peaks or valleys. It is therefore contemplated that the appended claims will cover any such modifications or embodiments.

All publications, patents and patent applications referred to herein are incorporated by reference in their entirety to the same extent as if each individual publication, patent or patent application was specifically and individually indicated to be incorporated by reference in its entirety.

What is claimed is:

1. A lamp device having a longitudinal axis, and comprising:
a first elongate electrical connector and a second elongate electrical connector, the first elongate electrical connector and the second elongate electrical connector being aligned in a spaced relationship with respect to a line orthogonal to the longitudinal axis, each of the first elongate electrical connector and the second elongate connector configured to form an oblique angle with respect to the longitudinal axis, ends of all of the electrical connectors of the lamp device being in substantial alignment along a plane orthogonal to the longitudinal axis.

2. The lamp device defined in claim 1, wherein the first elongate electrical connector and the second elongate electrical connector are substantially parallel with respect to one another.

3. The lamp device defined in claim 1, further comprising an elongate radiation emitting cavity comprising the longitudinal axis.

4. The lamp device defined in claim 1, wherein at least one of the first elongate electrical connector and the second elongate electrical connector comprises a male portion of a male-female connection system.

5. The lamp device defined in claim 1, wherein each of the first elongate electrical connector and the second elongate electrical connector comprises a male portion of a male-female connection system.

6. The lamp device defined in claim 1, wherein at least one of the first elongate electrical connector and the second elongate electrical connector comprises a male portion of a male-female connection system, and the other of the first elongate electrical connector and the second elongate electrical connector comprises a female portion of a male-female connection system.

7. The lamp device defined in claim 1, wherein each of the first elongate electrical connector and the second elongate electrical connector comprises a female portion of a male-female connection system.

8. The lamp device defined in claim 1, comprising a pair of first elongate electrical connectors and a pair of second elongate electrical connectors.

9. The lamp device defined in claim 8, wherein the pair of first elongate electrical connectors are in substantial alignment along a line orthogonal to the longitudinal axis.

10. The lamp device defined in claim 8, wherein the pair of second elongate electrical connectors are in substantial alignment along a line orthogonal to the longitudinal axis.

11. The lamp device defined in claim 8, wherein the pair of first elongate electrical connectors and the pair of second elongate electrical connectors are in substantial alignment along a line orthogonal to the longitudinal axis.

12. The lamp device defined in claim 1, wherein the first elongate electrical connector and the second elongate connector are disposed in a base portion at one end of the lamp device.

13. The lamp device defined in claim 12, wherein a cross-section of the base portion containing the longitudinal axis comprises an undulating shape.

14. The lamp device defined in claim 12, wherein a cross-section of the base portion containing the longitudinal axis comprises at least one peak and at least one valley.

15. The lamp device defined in claim 14, wherein the first elongate electrical connector and the second elongate electrical connector are offset with regard to the at least one peak or the at least one valley.

16. The lamp device defined in claim 14, wherein the first elongate electrical connector and the second elongate electrical connector are offset with regard to both of the at least one peak and the at least one valley.

17. The lamp device defined in claim 12, wherein a cross-section of the base portion containing the longitudinal axis comprises a single peak and a single valley.

18. The lamp device defined in claim 17, wherein the first elongate electrical connector and the second elongate electrical connector are offset with regard to the single peak or the single valley.

19. The lamp device defined in claim 17, wherein the first elongate electrical connector and the second elongate electrical connector are offset with regard to both of the single peak and the single valley.

20. The lamp device defined in claim 12, wherein a cross-section of the base portion containing the longitudinal axis comprises at a plurality of peaks and a plurality of valleys.

21. The lamp device defined in claim 20, wherein the first elongate electrical connector and the second elongate electrical connector are offset with regard to the plurality of peaks or the plurality of valleys.

22. The lamp device defined in claim 20, wherein the first elongate electrical connector and the second elongate electrical connector are offset with regard to both of the plurality of peaks and the plurality of valleys.

23. A lamp device having a longitudinal axis, and comprising:
a first elongate electrical connector and a second elongate electrical connector, the first elongate electrical connector and the second elongate electrical connector being aligned in a spaced relationship with respect to a line orthogonal to the longitudinal axis, each of the first elongate electrical connector and the second elongate connector configured to form an oblique angle with respect to the longitudinal axis, none of the elongate electrical connectors of the lamp device being staggered with respect to the longitudinal axis.

24. A lamp device having a longitudinal axis, and comprising:
a first pair of elongate electrical connectors and a second pair of elongate electrical connectors, the first pair of elongate electrical connectors and the pair of elongate electrical connectors being aligned in a spaced relationship with respect to a line orthogonal to the longitudinal axis, each of the elongate electrical connectors configured to form an oblique angle with respect to the longitudinal axis, ends of all of the electrical connectors being in substantial alignment along a plane orthogonal to the longitudinal axis.

* * * * *